(12) United States Patent
Byerly et al.

(10) Patent No.: US 11,771,828 B2
(45) Date of Patent: *Oct. 3, 2023

(54) MEDICATION DELIVERY DEVICE WITH MECHANICAL LOCKING SYSTEM

(71) Applicant: Eli Lilly and Company, Indianapolis, IN (US)

(72) Inventors: Roy Howard Byerly, Indianapolis, IN (US); Kimberly Ann Ringenberger, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,688

(22) Filed: Dec. 10, 2021

(65) Prior Publication Data

US 2022/0096751 A1    Mar. 31, 2022

Related U.S. Application Data

(63) Continuation of application No. 16/343,849, filed as application No. PCT/US2017/060509 on Nov. 8, 2017, now Pat. No. 11,229,743.

(Continued)

(51) Int. Cl.
*A61M 5/20* (2006.01)
*A61M 5/145* (2006.01)
(Continued)

(52) U.S. Cl.
CPC ............ *A61M 5/20* (2013.01); *A61M 5/1452* (2013.01); *A61M 5/2422* (2013.01);
(Continued)

(58) Field of Classification Search
CPC .... A61M 5/20; A61M 5/1452; A61M 5/2422; A61M 5/3155; A61M 5/14244;
(Continued)

(56) References Cited

U.S. PATENT DOCUMENTS 8,142,211 B2    3/2012    Bernstein et al.
8,435,394 B2    5/2013    Norgaard et al.
(Continued)

FOREIGN PATENT DOCUMENTS

WO    2014118105    8/2014
WO    2014118106    8/2014
(Continued)

OTHER PUBLICATIONS

Patent Cooperation Treaty International Search Report pertaining to International Application No. PCT/US2017/060509; dated Feb. 13, 2018.

*Primary Examiner* — Theodore J Stigell
(74) *Attorney, Agent, or Firm* — Arthur C. H. Shum

(57) ABSTRACT

A medication delivery device having a lock element. The device is connectable to an electrical plug of a conduit. The device includes an external housing with an opening that ports to a plug receiving hollow within an interior volume. An electrical circuit connected to at least one of a rechargeable battery and a memory controller includes a connection element within the plug receiving hollow. The lock element travels within the plug receiving hollow when a dose delivery assembly of the device operates for forcing medication from the device. The lock element is sized and positioned to have its travel halted by abutment with the plug, when the plug is within the plug receiving hollow and electrically interfacing with the connection element, to thereby halt the dose delivery assembly from further operating for forcing medication from the device.

6 Claims, 5 Drawing Sheets

Related U.S. Application Data

(60) Provisional application No. 62/422,160, filed on Nov. 15, 2016.

(51) Int. Cl.
  A61M 5/24 (2006.01)
  A61M 5/315 (2006.01)
  A61M 5/142 (2006.01)

(52) U.S. Cl.
  CPC ....... A61M 5/3155 (2013.01); A61M 5/14244 (2013.01); *A61M 2005/2073* (2013.01); *A61M 2005/31588* (2013.01); *A61M 2205/27* (2013.01); *A61M 2205/276* (2013.01); *A61M 2205/35* (2013.01); *A61M 2205/8206* (2013.01); *A61M 2205/8237* (2013.01); *A61M 2205/8262* (2013.01)

(58) Field of Classification Search
  CPC ........... A61M 2005/2073; A61M 2005/31588; A61M 2205/27; A61M 2205/276; A61M 2205/35; A61M 2205/8206; A61M 2205/8237; A61M 2205/8262
  See application file for complete search history.

(56) References Cited

U.S. PATENT DOCUMENTS

| | | | |
|---|---|---|---|
| 8,641,672 | B2 | 2/2014 | Yodfat et al. |
| 8,674,656 | B2 | 3/2014 | Iio et al. |
| 9,339,605 | B2 | 5/2016 | Wimpenny et al. |
| 9,381,297 | B2 | 7/2016 | Brown et al. |
| 10,064,996 | B2 * | 9/2018 | Draper ................ A61M 5/3204 |
| 10,173,005 | B2 * | 1/2019 | Draper .................... A61M 5/34 |
| 10,195,346 | B2 * | 2/2019 | Steel .................... A61M 5/3202 |
| 10,384,010 | B2 * | 8/2019 | Grubbe .................. A61M 5/20 |
| 11,229,743 | B2 * | 1/2022 | Byerly ............... A61M 5/2422 |
| 2014/0371668 | A1 * | 12/2014 | Welsch ............... A61M 5/1452 |
| | | | 710/62 |

FOREIGN PATENT DOCUMENTS

| | | |
|---|---|---|
| WO | 2014118109 | 8/2014 |
| WO | 2015091555 | 6/2015 |

* cited by examiner

MEDICATION DELIVERY DEVICE WITH MECHANICAL LOCKING SYSTEM

CROSS REFERENCE TO RELATED APPLICATIONS

This application is a continuation of U.S. application Ser. No. 16/343,849, filed Apr. 22, 2019, which is a National Stage of International Application No. PCT/US2017/060509, filed Nov. 8, 2017, which claims priority to U.S. Provisional Application No. 62/422,160, filed Nov. 15, 2016, the entire disclosures of all of which are hereby expressly incorporated by reference herein.

BACKGROUND OF THE INVENTION

The present invention pertains to medication delivery devices, and, in particular, to a mechanical locking system for a medication delivery device.

A variety of medication delivery devices, including for example pen injectors and infusion pumps, are commonly used for periodic administration of medications. Some of these devices may include electronics that use rechargeable batteries, and/or may have a capacity to download or upload data with an external computer element. Electrical cables that plug into these devices may be used to provide such recharging or data transfer capabilities.

To reduce the likelihood of electric shock to a device user, some devices are equipped with a feature that prevents a user from delivering medicine with such a device when it is plugged into an electrical cable. While useful, such device designs are not without their shortcomings, such as making it difficult or impossible to inspect the device's medication contents, or to change a needle on the device, when the device is plugged into the electrical cable.

Thus, it would be desirable to provide a medication delivery device that can overcome one or more of these and other shortcomings of the prior art.

BRIEF SUMMARY OF THE INVENTION

In one form thereof, the present invention provides a medication delivery device connectable to an electrical plug of a conduit for at least one of charging and data transfer. The medication delivery device includes: an external housing having an outer surface and defining an interior volume, the outer surface defining an opening that ports to a plug receiving hollow within the interior volume; a dose delivery assembly operable for forcing medication from the device; an electrical circuit within the interior volume connected to at least one of a rechargeable battery and a memory controller within the interior volume, the electrical circuit including a connection element within the plug receiving hollow for electrically interfacing with the plug when the plug is inserted, from external to the external housing, through the opening into the plug receiving hollow; a lock element within the interior volume operably connected to the dose delivery assembly to travel within the plug receiving hollow when the dose delivery assembly operates for forcing medication from the device, the lock element sized and positioned to have its travel halted by abutment with the plug, when the plug is within the plug receiving hollow and electrically interfacing with the connection element, to thereby halt the dose delivery assembly from further operating for forcing medication from the device.

One advantage of the present invention is that a medication delivery device with mechanical locking system may be provided that prevents a user from delivering a dose with it when connected to an electrical cable.

Another advantage of the present invention is that a medication delivery device with mechanical locking system may be provided that has a locking system that does not change the external appearance of the device.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
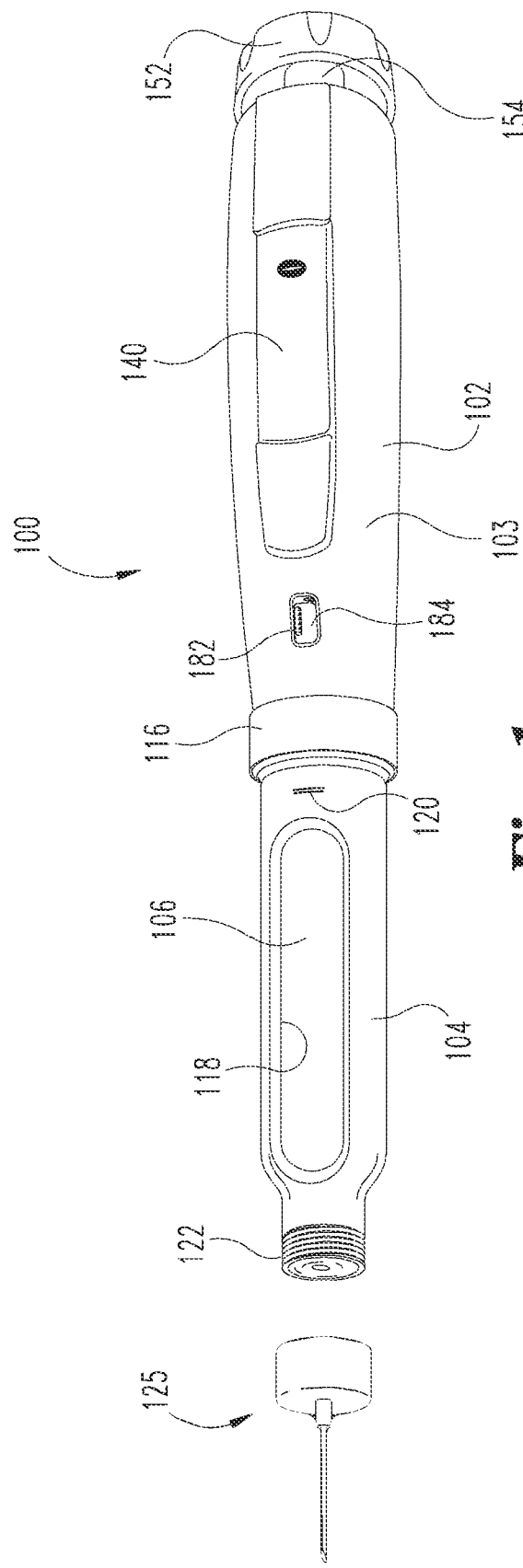
FIG. 1 is a perspective view of a medication delivery device in the form of an injection pen without a cap and prior to a mounting of a needle assembly.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION

Figure 2:
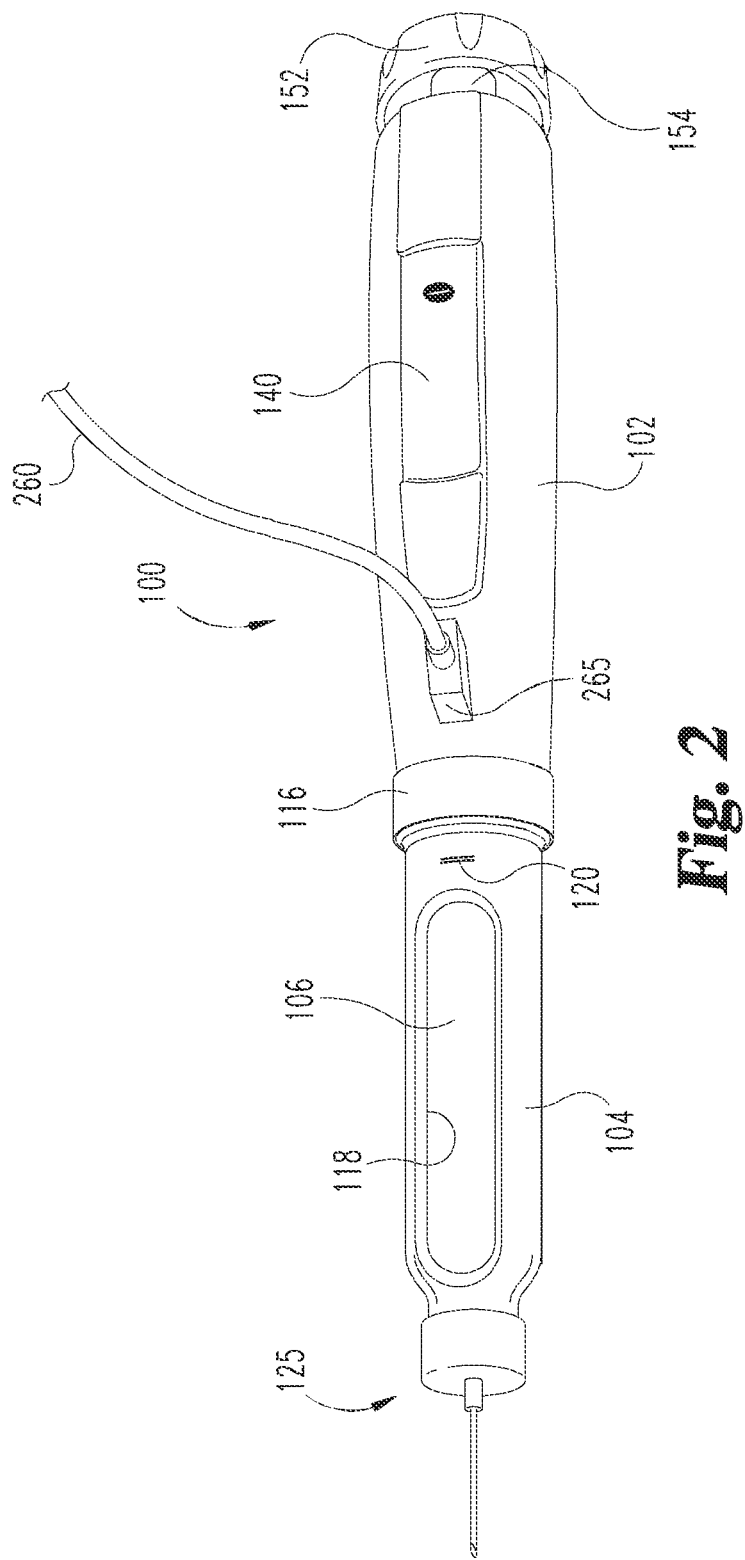
FIG. 2 is a perspective view of the medication delivery device of FIG. 1 with a needle assembly attached and with the plug of a partially shown electrical cable plugged into the device.
Figure 3:
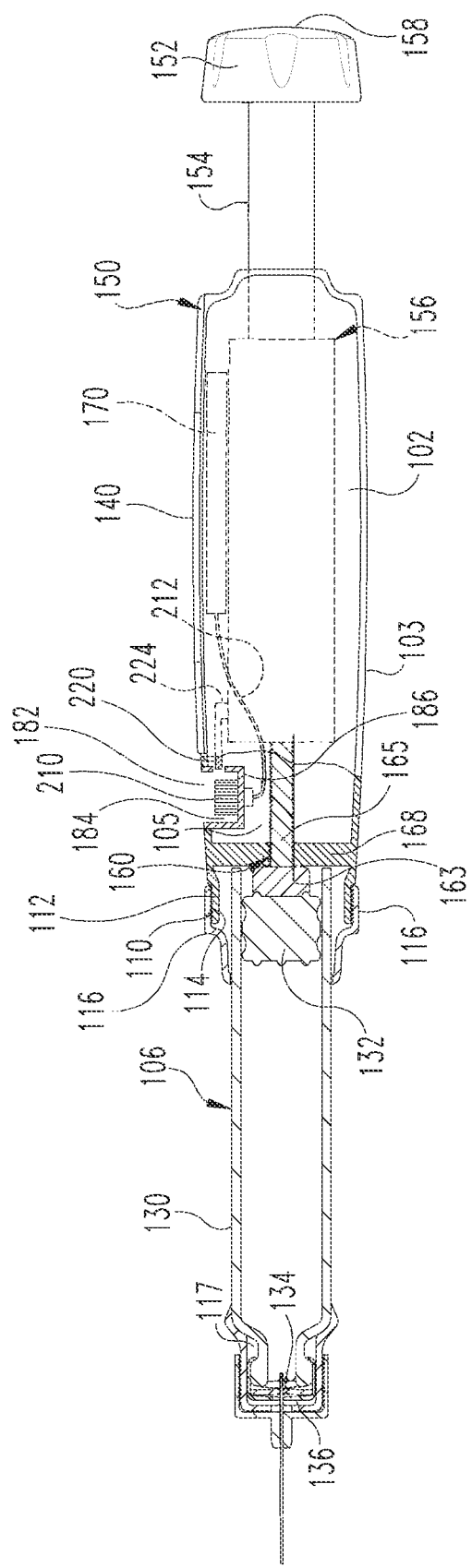
FIG. 3 is a side view in partial cross-section of the medication delivery device of FIG. 1 with a needle assembly attached after have been operated to set a dose for delivery.

Referring now to FIGS. 1-3, there is shown a medication delivery device equipped with a mechanical locking system that prevents the device from delivering a selected dose of medication when an electrical cable is plugged into the device. The shown device is a reusable pen-shaped medication injection device, generally designated 100, which is manually handled by a user to selectively set a dose and then to deliver, or inject, that set dose. Injection devices of this type are well known, and the description of device 100 is merely illustrative and not limiting as the mechanical locking system can be adapted for use in variously configured medication delivery devices, including differently constructed pen-shaped injection devices, differently shaped injection devices, and infusion devices. The medication may be any of a type that may be delivered by such a medication delivery device. Device 100 is similar in many respects to a device described in International Publication Number WO 02/092153, which publication is incorporated herein by reference in its entirety.

Medication injection device 100 includes an outer housing that supports the internal components of the device. The housing is shown as having a rear or main housing 102 and a forward or cartridge housing 104. Main housing 102 includes a volume 105 interior to the outer surface 103 of main housing 102 and in which is located a drive assembly of the device, which assembly is a strictly mechanical assembly as described but may in alternate embodiments be a motorized assembly. Cartridge housing 104, also known as the cartridge retainer, holds a cartridge 106 filled with medication to be delivered by device operation. Cartridge retainer 104 is detachably connectable or mountable to main housing 102 via external threading 110 on a protruding collar portion 112 of main housing 102 which mates with internal threading 114 on a ring portion 116 at the proximal end of cartridge retainer 104.

Cartridge retainer 104 includes an internal hollow 117 suited to removably receive cartridge 106, thereby allowing a cartridge to be inserted therein, and then removed therefrom when depleted and replaced with a fresh cartridge of similar design. Openings 118 in cartridge retainer 104 allow visibility of the cartridge contents. A detent feature 120 provided on the exterior of cartridge retainer 104 allows for a not shown protective cap to be detachably mounted over the cartridge retainer 104 when a needle assembly 125 is not attached to the cartridge retainer 104. Although cartridge retainer 104 is described herein as being a reusable component, the cartridge retainer 104 could be integrated with, and therefore be disposable with, the cartridge 106.

Medication cartridge 106 is of conventional design, including a barrel 130 having an interior reservoir filled with medication which is sealed at one end by a slidable plunger or piston 132 and sealed at the other end by a septum 134 held by a crimp ring 136.

A needle assembly 125 detachably mountable to an externally threaded distal end 122 of cartridge retainer 104 pierces the septum 134 when so mounted. The pierced septum through which the needle extends serves as an outlet during dispensing for the medication within the reservoir of barrel 130, which medication is delivered through the needle assembly 125 by operation of device 100. The cartridge 106 can hold multiple doses of medication, or even a single dose, depending on the purpose of device 100.

Medication injection device 100 is shown in FIGS. 1 and 2 in its "zero position" at which the device has not been set for delivery of any dose. This zero position setting is indicated by the number "0" visible on the electronic dose display 140 in FIG. 1. In FIG. 3, device 100 is arranged after being manipulated to set a dose of thirty units for delivery, and before that device 100 is being operated to deliver that set dose. For the device in FIG. 3, the number "30" would be visible on the display 140.

With reference to FIG. 3, medication injection device 100 is typical of many such reusable devices in including a manually-powered dose delivery mechanism or assembly, generally designated 150, operable to force medicine within the cartridge 106 through the needle assembly 125 to deliver a dose. The dose delivery mechanism 150 includes a drive member, generally designated 160, that advances within the cartridge barrel 130 in a forward axial direction to directly engage and advance plunger 132. Dose delivery mechanism 150 includes a mechanical drive assembly abstractly indicated at 156 that is housed within main housing 102 and acts directly on drive member 160. Dose delivery mechanism 150 includes a dose knob 152 connected via a tube 154 to mechanical drive assembly 156. When knob 152 is turned by a user to set a dose for injection, dose knob 152 and tube 154 screw out together from main housing 102 in a rearward axial direction. When a user applies a suitable axial plunging force on the proximal end 158 of dose knob 152, the resulting simply translational motion of dose knob 152 and tube 154 axially forward into main housing 102 is converted by drive assembly 156 into a smaller motion of drive member 160 forward from main housing 102 into the interior of cartridge barrel 130 to deliver a dose of medication from the device.

Drive member 160 is formed in two pieces including a forward end 163 that directly engages the cartridge plunger 132, and a shaft 165 that axially extends rearward from forward end 163 into main housing 102. The shaft 165 is threaded and is engaged with drive assembly 156 to be screwed out from main housing 102 as it is rotated to be driven forward. Shaft 165 is shown threadedly engaged with a housing bulkhead 168, which housing bulkhead is shown integral with main housing 102 but could be separately formed and fixedly attached thereto. Forward end 163 is provided in the form of an enlarged diameter foot that is mounted on shaft 165 to allow relative rotation, allowing foot 163 to engage plunger 132 without relative rotation therebetween as shaft 165 screws out. While this foot and shaft two-piece construction of drive member 160 is preferred when shaft 165 screws out from the housing during advancement, such a construction is not required in devices, particularly if the drive member simply translates as it is forced forward from the housing, in which case a single piece drive member construction may be more acceptable.

Device 100 uses an electronic dose display 140 circuited to and controlled by an electronic controller or computing assembly 170 mounted within main housing 102. Controller 170 may include conventional components such as a microprocessor, battery, memory, etc. Controller 170 is programmed to achieve the electronic features of device 100, including causing the display of set doses and communicating with an external computer element, whether it be wirelessly or via a wired connection. The set dose displayed in display 140 as device 100 is prepared for an injection, and the amount of medicine remaining to be injected displayed in display 140 during an injection, are determined by the interaction of dose delivery mechanism 150 with not shown sensing systems within the device 100 that are electrically circuited with controller 170.

Device 100 is configured to receive an electrical plug 250 of an external electrical cable or conduit 260. Main housing surface 103 includes an uncovered opening 182 that ports to a hollow 184 located within interior volume 105 which is of a size and shape suitable to receive the conduit plug 250. In the shown embodiment, hollow 184 is within the internal space bounded by the interior surfaces of the walls of a plug socket 186 secured to main housing 102. An electrical connector or connection element 210 on socket 186 extends within hollow 184 and is wired to a conduit 212 within the housing interior volume 105. Conduit 212 is shown circuited to controller 170 in general.

Figure 6:
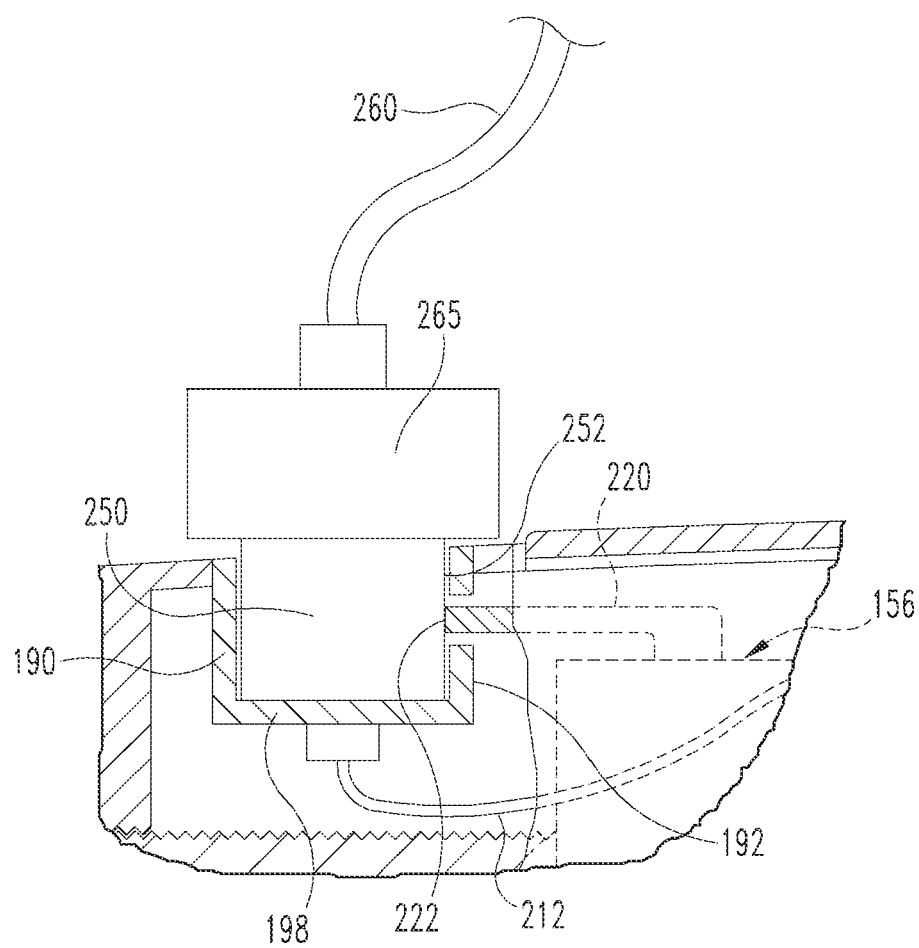
FIG. 6 is a cross-sectional side view of a portion of the medication delivery device of FIG. 2 showing the abutment of the lock pin with the inserted plug, which plug is not shown in cross-section, that prevents the device from delivering medication.

Connection element 210 electrically interfaces with the plug 250 when plug 250 is inserted from external to the external housing 102 through opening 182 into the hollow 184 as shown in FIG. 6. Opening 182 and hollow 184 are configured for plug 250 to be insertable into the device. Such insertion need not be, but may be, in a direction generally perpendicular to the housing 102 at opening 182. The component(s) of controller 170 to which the conduit 212 connects may be the rechargeable battery, if the plug 250 is used for device charging, and/or the memory controller, which may or may not be part of the microprocessor, if the plug 250 is used for data transfer.

The plug socket walls include angled end walls 190, 192, opposite side walls 194, 196 and an internal base wall 198. Socket 186 is shown having an end in the radially outward direction which is formed by outward faces 200, 201, 202 and 203 of end walls 190, 192 and side walls 194, 196 and which is generally flush with housing surface 103. The socket 186 may protrude outward beyond or be recessed inward from the surface 103 within the scope of the invention. The size and positioning of socket walls 190, 192, 194, 196 and 198 need not closely conform to the size and shape of the plug 250. Furthermore, while socket 186 bounds the hollow 184 that receives the male shaped plug 250 in the shown embodiment, the socket is not required if a suitable support for the connection element 210 for electrically interfacing with plug 250 is otherwise provided within housing 102. Such an alternate construction may be provided by having the connection element 210 of the device be included in a male plug secured to an interior portion of the housing so that the male plug is fully contained within the housing interior 105, and having the plug of the external cable be provided as a female plug that when installed mounts over the male plug within interior volume 105.

Socket end wall 192 includes an aperture or hole 215 sized to allow passage of a lock element 220 that is operably connected to the dose delivery mechanism 150. Lock element 220 is shiftably mounted within the housing interior volume 105. The lock element 220 is shown provided in the shape of a cylindrical rod or pin having an axial length extending between a forward end face 222 and a rearward end 224. Rearward end 224 is shown in FIG. 3 connected to the mechanical drive assembly 156 so that lock element 220 projects axially forward from drive assembly 156 toward socket 186. Lock element 220 may be additionally supported by a complementarily designed housing wall or apertured housing structure or bulkhead.

The connection of lock element 220 with dose delivery mechanism 150 may be direct or indirect so long as an operable connection results in which axial movement of lock element 220 follows from a movement of dose delivery mechanism 150 necessary to deliver a set dose. For example, the operable connection may be a direct connection, such as lock pin 220 being acted on immediately, or directly attached to, a component of the dose delivery mechanism that moves in order to advance the cartridge plunger 132. The operable connection alternatively may be an indirect connection, such as lock pin 220 being acted on or directly attached to a part that itself, or via one or more additional intervening parts, is being acted on by a component of the dose delivery mechanism that moves in order to advance the cartridge plunger 132. One suitable direct connection is to have the lock pin 220 be acted on and shifted axially forward by a member of drive assembly 156 that during non-plugged in use, after its initial axial motion that so moves the lock pin 220, directly rotates the threaded shaft 165 to cause that shaft to be screwed out from main housing 102. One suitable indirect connection is to have lock pin 220 extend from a trolley axially movable within the housing, and which trolley holds sensor components for sensing motion of one or more members of drive assembly 156, which trolley may be axially shifted by contact with a member of the drive assembly when the drive assembly is operating, but which trolley itself is not necessary to convert a plunging motion of dose knob 152 into advancement of cartridge plunger 132.

Lock element 220 moves axially forward when device 220 is being operated for forcing medication from device 100. Lock element 220 does not move axially when device 100 is being operated for setting a dose for delivery. In one embodiment of device 100, the lock element 220 is shifted axially forward during a first phase of the device operation for forcing medication from the device. This first phase is a transitory phase during which the mechanical drive assembly 156 translates axially forward within main housing 102 during the injection process before the assembly 156 starts to drive the drive member 160 forward. The lock element 220 does not move further axially forward after the first phase is completed and when the drive member 160 is advanced forward during the second phase of the device operation for forcing medication from device 100. In an alternate design in which the device does not have a transitory phase, the locking pin 220 is moved axially forward simultaneously with the axially forward movement of the drive member 160.

Figure 4:
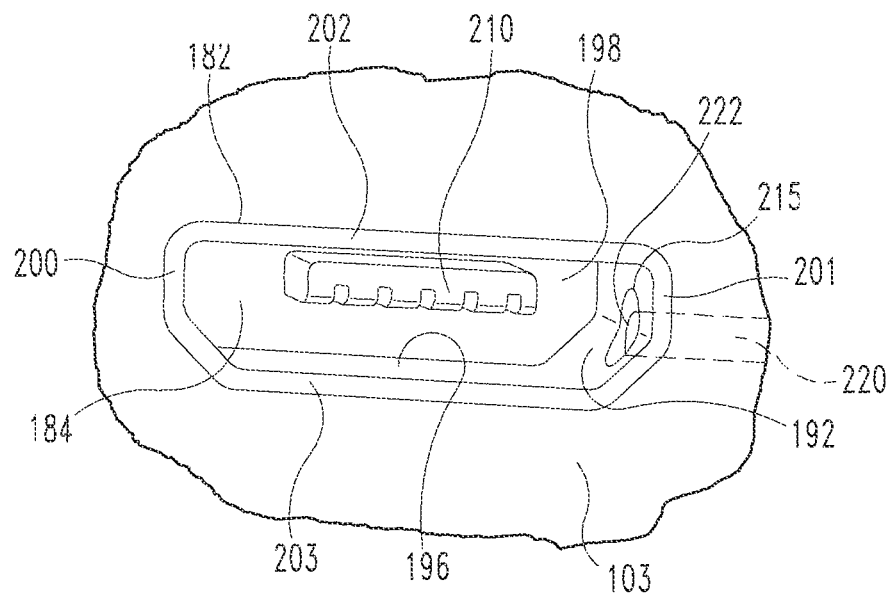
FIG. 4 is a partial, perspective view of an exterior portion of the medication delivery device of FIG. 1 when not plugged into an electrical cable and not being used to deliver a dose of medication, where a portion of a lock pin otherwise hidden within the device interior is shown in dashed lines.
Figure 5:
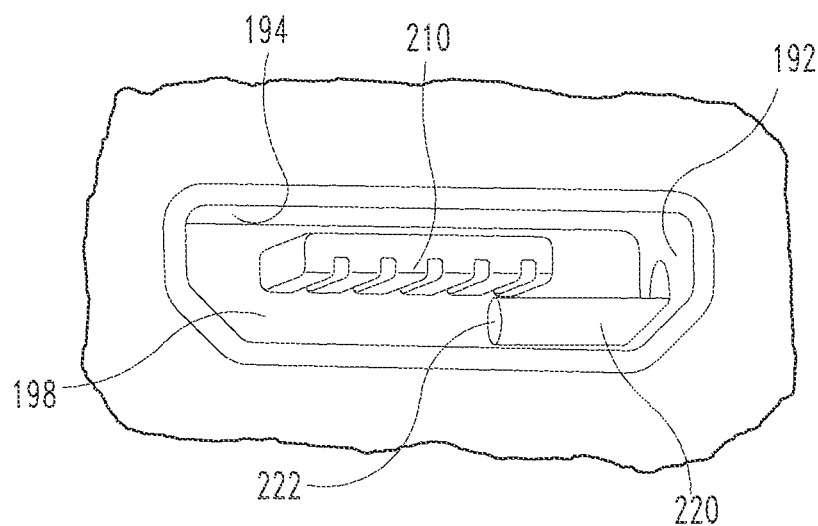
FIG. 5 is a partial, perspective view similar to FIG. 4 when the medication delivery device of FIG. 1 is not plugged into an electrical cable and is being used to deliver a dose of medication.

With reference to FIGS. 3 and 4, when device 100 is not being operated to force medication from cartridge 106, lock pin 220 is in a static, retracted position and does not project within hollow 184 or the internal space bounded by the walls of plug socket 186. When in this retracted position, lock pin 220 has its forward end face 222 located within wall hole 215. When device 100 is not plugged in and is being operated to force medication from cartridge 106, lock pin 220 advances axially forward into hollow 184 into the space between connection element 210 and side wall 196 as shown in FIG. 5. In FIG. 5, the lock pin 220 is shown after being fully advanced forward to its final inserted pin position during use mode for that embodiment. In other embodiments, the distance of total travel may be different. For device 100, lock pin 220 moves into this position during the first phase of delivery operation described above, after which no further axial movement occurs until a user removes the plunging force from proximal end 158 of dose knob 152, allowing the lock pin 220 to axially return to the retracted position shown in FIGS. 3 and 4. The lock pin return to the retracted position may be caused by one or more design configurations, such as an operable connection with the dose delivery mechanism that pulls the lock pin rearward, or the use of a biasing member acting between, for example, the lock pin 220 and the housing.

Device 100 is shown in FIG. 2 receiving plug 250, with an electrical conduit or cable 260 extending from the plug finger grip 265 from which plug 250 extends. The electrical conduit 260 with plug 250 can perform one or more of a variety of known functions. The electrical conduit 260 may be connected to a power supply at its end opposite the end with plug 250 and serve to provide an electrical charging of a rechargeable battery of device controller 170. The electrical conduit 260 may be connected to a computing element at its end opposite the end with plug 250, either directly or through one or more further networked connections, and could serve to download or upload data, such as device use or device programming instructions, to or from the memory of device controller 170.

As shown in FIG. 6, when plug 250 has been inserted within the plug receiving hollow 184 and electrically interfacing with the connection element 210, the travel path for lock pin 220 within hollow 184 is blocked. When a user attempts to operate device 100 to deliver a dose with plug 250 so inserted, axial motion forward of lock pin 220 is halted by direct abutment of pin end face 222 with the end or short side surface 252 of plug 250. The halting of lock pin 220 halts dose delivery mechanism 150 from further operation for forcing medication from device 100. In this way, a user is prevented from delivering a dose so long as plug 250 is so inserted. When plug 250 is subsequently removed from hollow 184, the travel path blockage of lock pin 220 is removed, allowing device 100 to again be operated to deliver medication.

The shown lock pin configuration is representative of a suitable locking system, but other lock elements may be used. For example, the lock element could be shaped other than a projecting pin, such as a shoulder that fits within a larger opening or slot in the socket. Additionally, the lock element could be operatively connected to the dose delivery mechanism by being integrally formed with a portion of a member of that dose delivery mechanism. Still further, while the lock element as described above is a dedicated part in that it has no function other than its locking function described above, the lock element need not be so dedicated and may be a component of another device system, such as by being a functionally essential portion of a member of the dose delivery mechanism. Still further, while the lock element is shown as moving in an axial direction, in an alternate embodiment the lock element can be configured to move in a different direction, such as radially or at an angle, and also alternatively can be designed to move rotationally or about a pivot point rather than in a straight path as described above.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. A medication delivery device connectable to an electrical plug of a conduit for at least one of charging and data transfer, the medication delivery device comprising:
    an external housing having an outer surface and defining an interior volume, said outer surface defining an opening that ports to a plug receiving hollow within said interior volume;
    a reservoir configured to be filled with a medication;
    a plunger operable for forcing the medication from the reservoir by advancing within the reservoir;
    an electrical circuit within said interior volume connected to at least one of a rechargeable battery and a memory controller within said interior volume, said electrical circuit including an electrical connector within said plug receiving hollow for electrically interfacing with the plug when the plug is inserted, from external to the external housing, through the opening into the plug receiving hollow;
    a lock element within said interior volume operably connected to said plunger to travel within said plug receiving hollow when said plunger operates for forcing medication from the medication delivery device, said lock element sized and positioned to have its travel halted by abutment with the plug, when the plug is within the plug receiving hollow and electrically interfacing with said electrical connector, to thereby halt said plunger from further operating for forcing the medication from the medication delivery device.

2. The medication delivery device of claim 1 wherein said lock element extends through an aperture in a wall of a socket that defines said plug receiving hollow.

3. The medication delivery device of claim 2 wherein said lock element does not extend within said plug receiving hollow when said plunger is not being operated.

4. The medication delivery device of claim 1 wherein the reservoir is a barrel of a medication cartridge, the medication delivery device further comprising a drive member that is shiftable in an axial direction within the barrel of the medication cartridge, and wherein said lock element travels in said axial direction within said plug receiving hollow.

5. The medication delivery device of claim 4 wherein said opening and plug receiving hollow are configured for the plug insertion in a direction generally perpendicular to the axial direction.

6. The medication delivery device of claim 1 wherein the reservoir is filled with the medication.

\* \* \* \* \*